(12) United States Patent
Jones et al.

(10) Patent No.: US 11,118,943 B2
(45) Date of Patent: Sep. 14, 2021

(54) SENSOR DEVICE REMOVABLY ATTACHABLE TO A DRUG DELIVERY DEVICE

(71) Applicant: Sanofi-Aventis Deutschland GMBH, Frankfurt am Main (DE)

(72) Inventors: Matthew Jones, Warwick (GB); Samuel Steel, Warwick (GB); Barry Yates, Warwickshire (DE); Anthony Paul Morris, Coventry (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 16/785,887

(22) Filed: Feb. 10, 2020

(65) Prior Publication Data

US 2020/0173815 A1 Jun. 4, 2020

Related U.S. Application Data

(63) Continuation of application No. 16/265,700, filed on Feb. 1, 2019, now Pat. No. 10,598,518, which is a (Continued)

(30) Foreign Application Priority Data

Jun. 10, 2014 (EP) .................................. 14171717

(51) Int. Cl.
*G01D 5/34* (2006.01)
*A61M 5/168* (2006.01)
(Continued)

(52) U.S. Cl.
CPC ............. *G01D 5/34* (2013.01); *A61M 5/1685* (2013.01); *A61M 5/31525* (2013.01); (Continued)

(58) Field of Classification Search
CPC ............ G01D 5/34; G01D 5/30; G01D 5/342; A61M 5/31553; A61M 5/1685; (Continued)

(56) References Cited

U.S. PATENT DOCUMENTS 5,523,560 A 6/1996 Manique et al.
5,766,155 A 6/1998 Hyman et al.
(Continued)

FOREIGN PATENT DOCUMENTS

CN 1671432 9/2005
CN 101522239 9/2009
(Continued)

OTHER PUBLICATIONS

International Search Report and Written Opinion in International Application No. PCT/EP2015/062769, dated Aug. 5, 2015, 12 pages.
(Continued)

*Primary Examiner* — Seung C Sohn
(74) *Attorney, Agent, or Firm* — Fish & Richardson P.C.

(57) ABSTRACT

A sensor device is removably attachable to a drug delivery device. The sensor device comprises an array of optical sensors arranged within the sensor device such that, when the sensor device is attached to the drug delivery device, which has a first movable element configured to move along a path parallel to the longitudinal axis of the drug delivery device, each optical sensor is operable to detect light received at different locations along the path and to output a signal indicative of an amount of detected light. Circuitry is configured to receive the signals output from the optical sensors and, based on the received signals, determine information associated with a location along the path of the first movable element.

21 Claims, 12 Drawing Sheets

Related U.S. Application Data continuation of application No. 15/316,765, filed as application No. PCT/EP2015/062769 on Jun. 9, 2015, now Pat. No. 10,228,268.

(51) Int. Cl.
   *A61M 5/315* (2006.01)
   *G01D 5/30* (2006.01)
   *A61M 5/31* (2006.01)

(52) U.S. Cl.
   CPC .......... *A61M 5/31553* (2013.01); *G01D 5/30* (2013.01); *A61M 2005/3126* (2013.01); *A61M 2205/3306* (2013.01); *A61M 2205/3379* (2013.01); *A61M 2205/3389* (2013.01); *A61M 2205/52* (2013.01); *A61M 2205/6063* (2013.01); *A61M 2205/6072* (2013.01); *G01D 5/342* (2013.01)

(58) Field of Classification Search
   CPC ...... A61M 5/31525; A61M 2005/3126; A61M 2205/6072; A61M 2205/52; A61M 2205/3389; A61M 2205/3379; A61M 2205/3306; A61M 2205/6063
   See application file for complete search history.

(56) References Cited

U.S. PATENT DOCUMENTS

| | | | |
|---|---|---|---|
| 5,819,726 A * | 10/1998 | Rubsamen | A61M 15/0045 128/200.14 |
| 7,498,563 B2 | 3/2009 | Mandro et al. | |
| 8,197,449 B2 | 6/2012 | Nielsen | |
| 8,221,356 B2 | 7/2012 | Enggaard | |
| 8,512,296 B2 | 8/2013 | Gabriel et al. | |
| 9,358,344 B2 * | 6/2016 | Pala | A61M 5/31525 |
| 9,474,864 B2 * | 10/2016 | Leary | A61M 5/31586 |
| 2006/0224123 A1 | 10/2006 | Friedli et al. | |
| 2009/0299279 A1 | 12/2009 | Richter | |
| 2013/0072897 A1 * | 3/2013 | Day | G06K 7/10 604/500 |
| 2014/0051182 A1 | 2/2014 | Reichmuth et al. | |
| 2014/0194825 A1 | 7/2014 | Nielsen et al. | |
| 2015/0306304 A1 | 10/2015 | Schabbach et al. | |

FOREIGN PATENT DOCUMENTS

| | | |
|---|---|---|
| CN | 102905613 | 1/2013 |
| CN | 103702699 | 4/2014 |
| JP | 2007-506470 | 3/2007 |
| JP | 2010-505475 | 2/2010 |
| JP | 2013-039450 | 2/2013 |
| JP | 2013-505433 | 2/2013 |
| JP | 2013-521963 | 6/2013 |
| WO | WO 2004/009163 | 1/2004 |
| WO | WO 2005/004955 | 1/2005 |
| WO | WO 2006/120182 | 11/2006 |
| WO | WO 2008/145171 | 12/2008 |
| WO | WO 2011/032960 | 3/2011 |
| WO | WO 2011/117212 | 9/2011 |
| WO | WO 2013/004844 | 1/2013 |
| WO | WO 2013/010886 | 1/2013 |
| WO | WO 2013/066194 | 5/2013 |
| WO | WO 2013/110538 | 8/2013 |
| WO | WO 2014/052137 | 4/2014 |
| WO | WO 2014/161953 | 10/2014 |
| WO | WO 2015/189173 | 12/2015 |

OTHER PUBLICATIONS

International Preliminary Report on Patentability in International Application No. PCT/EP2015/062769, dated Dec. 15, 2016, 8 pages.

* cited by examiner

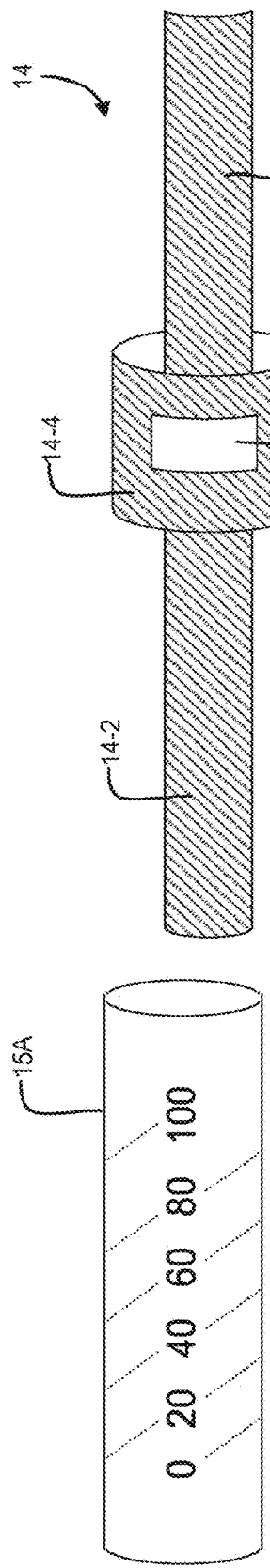
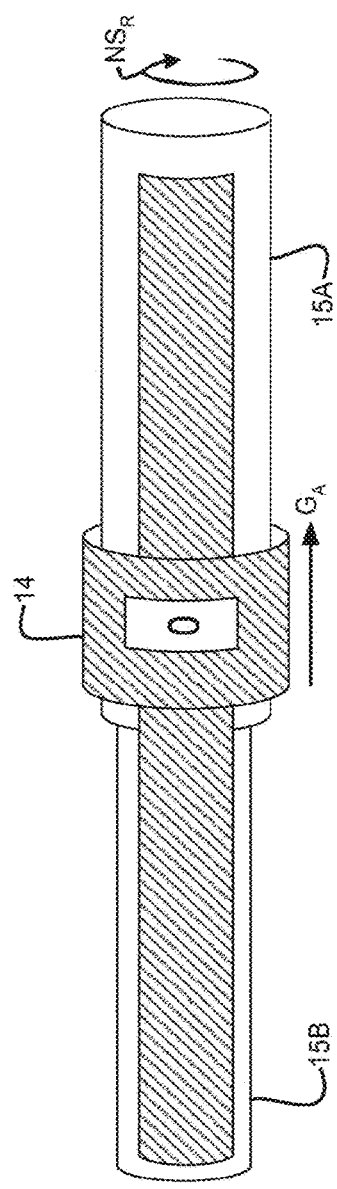
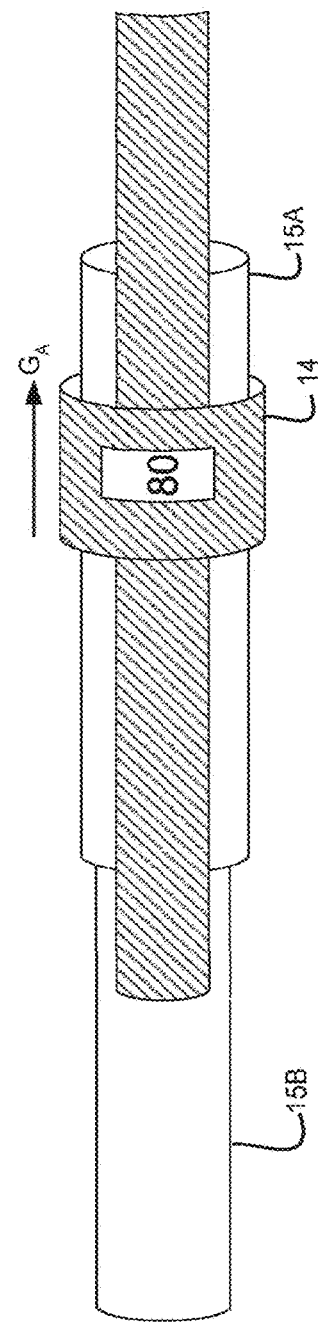
FIGURE 2A
FIGURE 2B
FIGURE 2C
FIGURE 2D

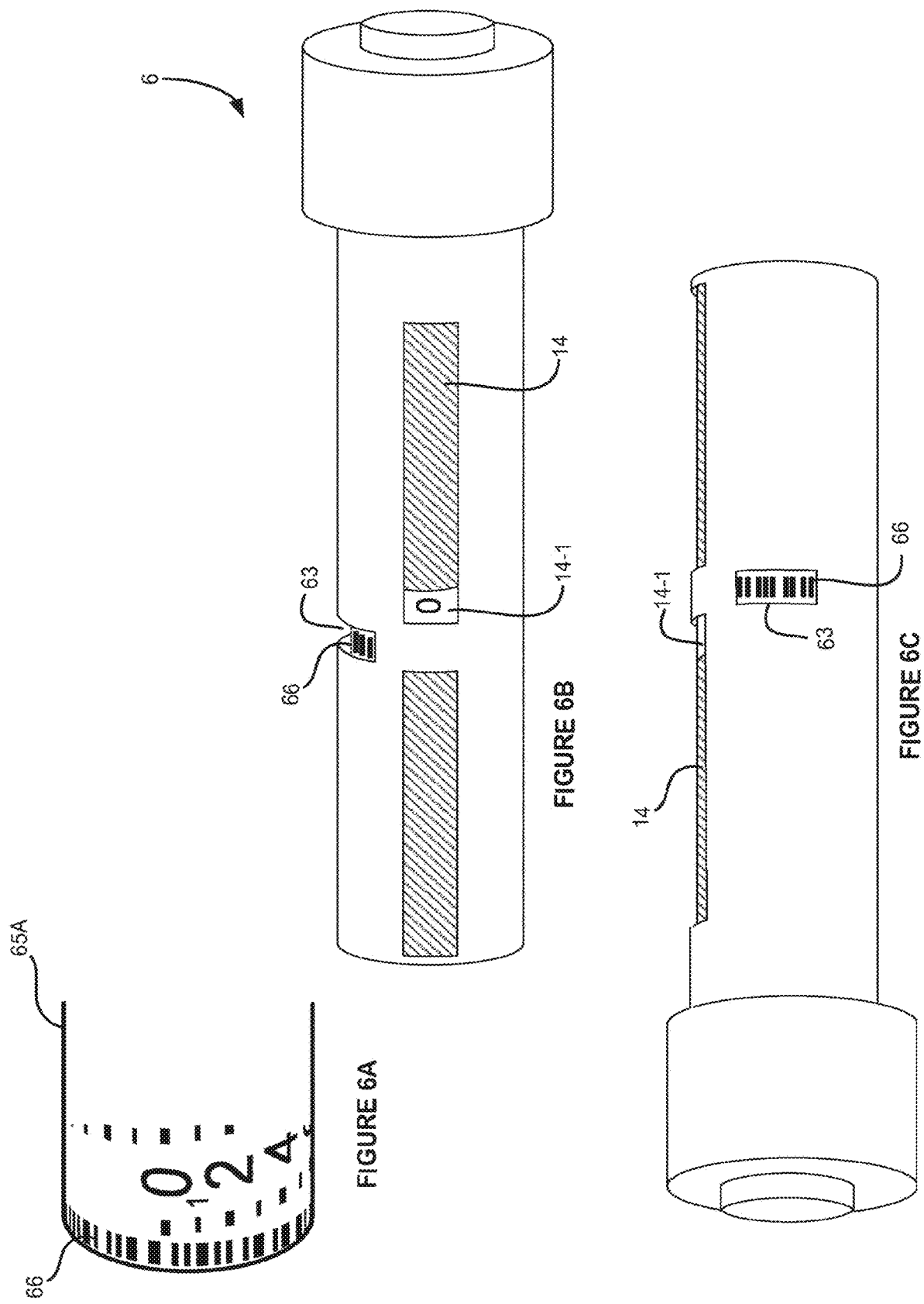

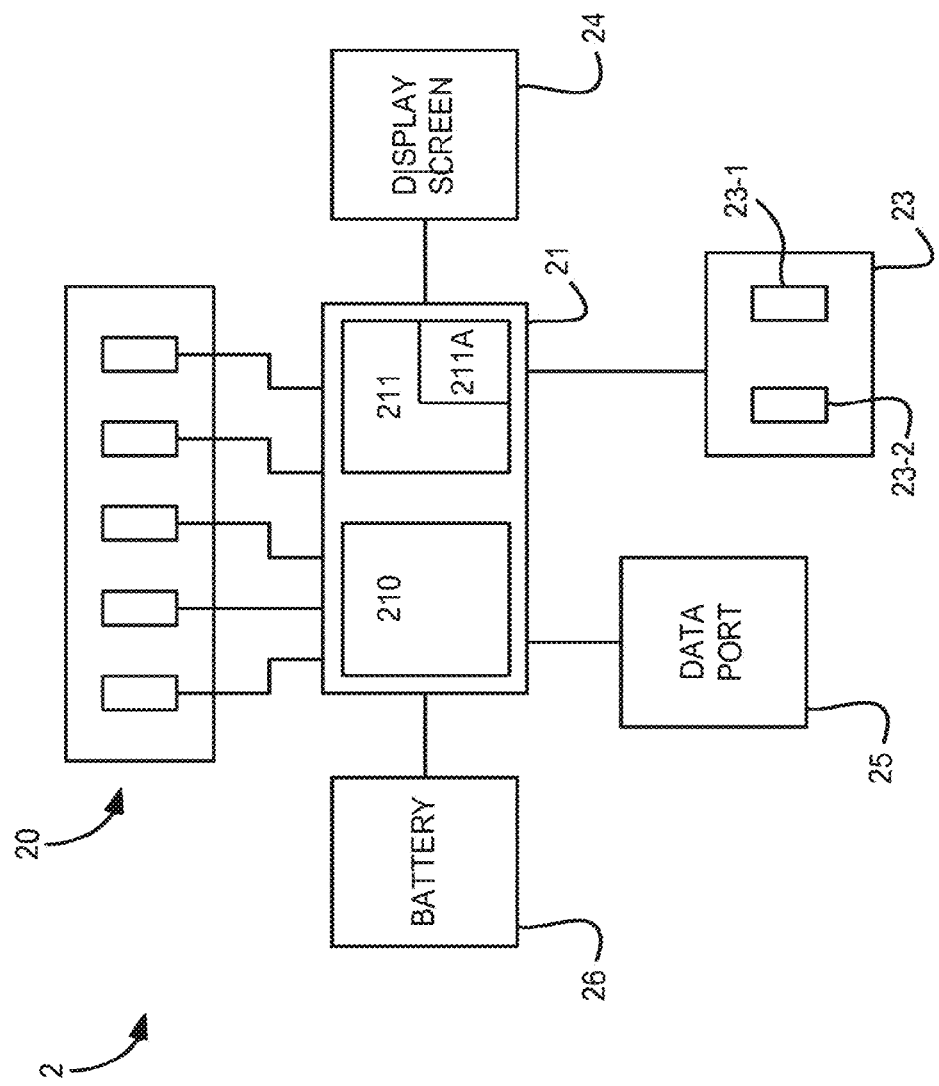

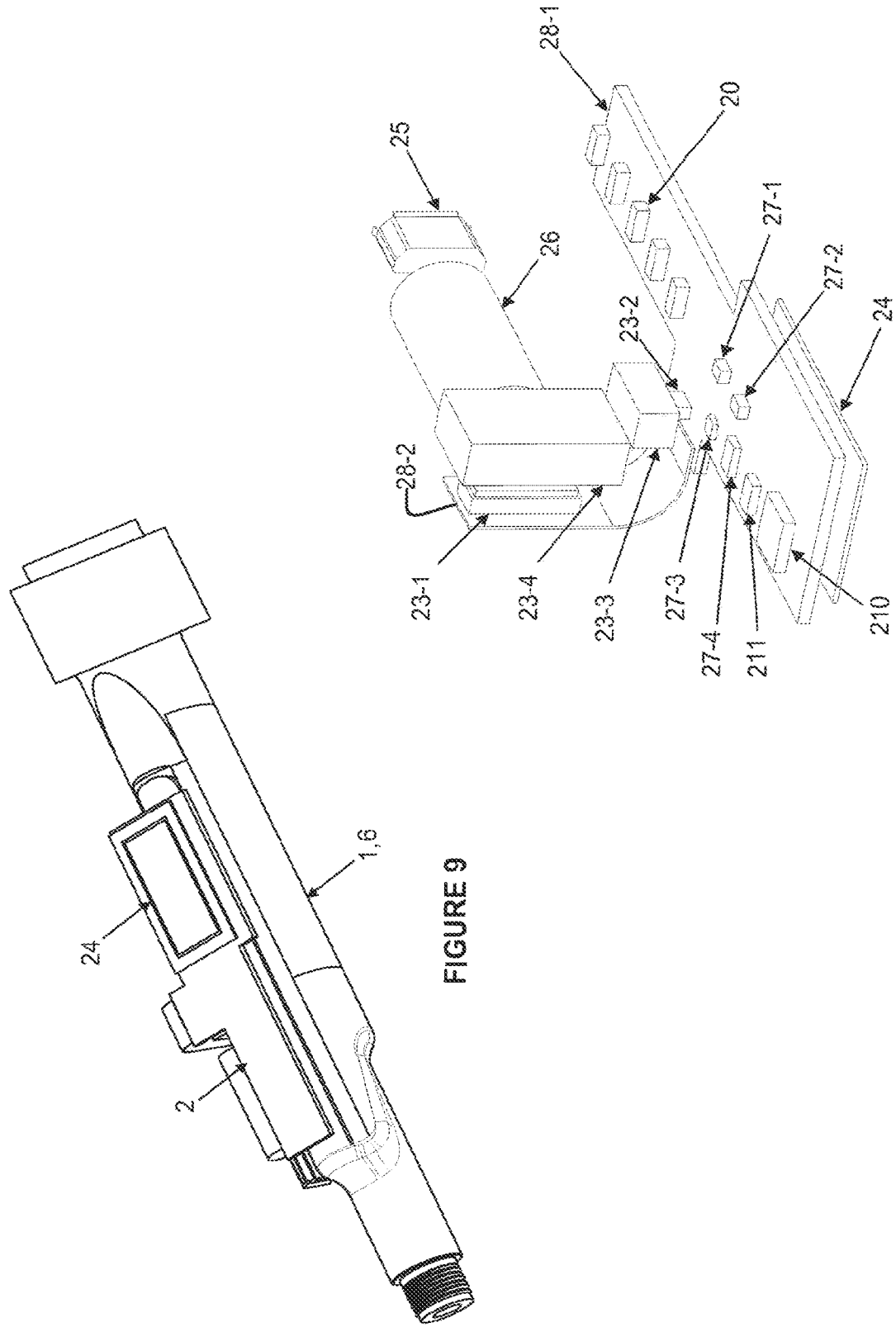

SENSOR DEVICE REMOVABLY ATTACHABLE TO A DRUG DELIVERY DEVICE

CROSS-REFERENCE TO RELATED APPLICATIONS

This application is a continuation of U.S. patent application Ser. No. 16/265,700, filed on Feb. 1, 2019, which is a continuation of U.S. patent application Ser. No. 15/316,765, filed on Dec. 6, 2016, now U.S. Pat. No. 10,228,268, which is a U.S. national stage application under 35 USC § 371 of International Application No. PCT/EP2015/062769, filed on Jun. 9, 2015, which claims priority to European Patent Application No. 14171717.3 filed on Jun. 10, 2014, the entire contents of which are incorporated herein by reference.

FIELD

The disclosure relates to a sensor device removably attachable to a drug delivery device such as an injection pen.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning (dialling) a dosage knob and observing the actual dose from a dose window or display of the insulin pen. The dose is then injected by inserting the needle into a suited skin portion and pressing an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin type and dose.

It has been described, for instance in WO 2011/117212, to provide a supplementary device comprising a mating unit for releasably attaching the device to an injection/drug delivery device. The device includes a camera and is configured to perform optical character recognition (OCR) on captured images visible through a dosage window of the injection pen, thereby to determine a dose of medicament that has been dialled into the injection device. In order for such a supplementary device to successfully determine the dose, the dosage window must remain stationary. However not all drug delivery devices operate in this way.

SUMMARY

According to a first aspect of the disclosure there is provided a sensor device removably attachable to a drug delivery device, the sensor device comprising:
an array of optical sensors arranged within the sensor device such that, when the sensor device is attached to the drug delivery device, the drug delivery device having a first movable element which is configured to move along a path parallel to the longitudinal axis of the drug delivery device, each optical sensor is operable to detect light received at different locations along the linear path and to output a signal indicative of an amount of detected light; and
circuitry configured to receive the signals output from the optical sensors and, based on the received signals, to determine information associated with a location along the path of the first movable element.

This can allow detection of the approximate longitudinal position of the movable element of the drug delivery device with a relatively simple arrangement in the sensor device. The rotational position of the moveable element or a related element can be detected through a separate sensor arrangement.

Each of the optical sensors may have a corresponding light source arranged to emit light towards the externally visible path when the sensor device is attached to the drug delivery device, each of the optical sensors being arranged to detect the emitted light reflected from the externally visible path.

Each of the optical sensors may be a PIN diode, for instance.

The array of optical sensors may be arranged within the sensor device such that, when the sensor device is attached to the drug delivery device, the optical sensors of the array are generally equidistantly spaced from one another along a length corresponding to the length of the visible path.

The array of optical sensors may extend generally along an axis.

When the sensor device is attached to the drug delivery device, the axis along which the array of optical sensors may extend may be generally parallel to a longitudinal axis of the drug delivery device.

The sensor device may comprise:
a sensing arrangement arranged within the sensor device such that, when the sensor device is attached to the drug delivery device, the sensing arrangement is operable to read encoded information that is externally visible on the drug delivery device, wherein the circuitry is configured to determine, based on the encoded information, information relating to operation of the drug delivery device.

Here, the circuitry may be configured to determine based on the encoded information and the location along the path of the first movable element, information relating to a drug dose to which the drug delivery device is currently dialled.

Optionally, at least part of the encoded information is provided on at least a second movable element of the drug delivery device, the second movable element being rotatable within the drug delivery device and wherein the circuitry is configured to determine based on the encoded information a degree of rotation of the second movable element within the drug delivery device. The circuitry may be configured to determine the information relating to currently-dialled drug dose based on the location along the visible path of the first movable element and the degree of rotation of the second movable element.

The movement of the first and second movable elements may be interdependent.

The circuitry may be configured to determine based on the encoded information an operational mode of the drug delivery device.

The encoded information may be dependent on a position of a further movable element within the drug delivery device, the position of which may be dependent on whether the drug delivery device is in dialling mode or dispensing mode.

The circuitry may be configured to determine based on the encoded information a drug for which the drug delivery device is being used to dispense.

At least part of the encoded information may be externally visible through an aperture or window formed in the delivery device, wherein the sensing arrangement is arranged within the sensor device such that, when the sensor device is attached to the drug delivery device, the sensing arrangement is operable to detect light received from the aperture or window. Here, the sensing arrangement may comprise:

- a light source arrangement configured to project light towards the aperture or window in the drug delivery device when the sensor device is attached to the drug delivery device; and
- a photosensor arrangement configured to receive light reflected from the aperture or window.

The light source arrangement may comprise a light source and a light guide arranged together to project light towards the aperture or window in the drug delivery device.

The photosensor arrangement may comprise a photosensor configured to receive light the aperture or window and one or more lenses configured to focus an image of the aperture or window towards the photo-sensor.

Another aspect of the disclosure provides a drug delivery system comprising:

- the sensor device above; and
- the drug delivery device having the first movable element which is configured to move along the externally visible path.

The first movable element may be moveable along an underlying element and is configured such that movement of the first movable element in a particular direction causes the underlying element to become visible at successive locations along the externally visible path, wherein at least part of the first movable element has a first reflectance and the underlying element has a second, different reflectance.

The first moveable element may be movable relative to the underlying element such that movement in a first direction along the externally visible path causes an increasing length of the underlying element to become visible in the externally visible path.

Alternatively, the first moveable element may comprise a first region having the first reflectance and a window or aperture provided in the first region through which the underlying element is externally visible.

The drug delivery device may comprise:

- a drug dispensing mechanism, actuation of which causes the drug to be dispensed to the user; and
- a further movable element configured to be movable from a first position to a second position in response to actuation of the drug dispensing mechanism, a first part of the further movable element being externally visible through a window or aperture of the drug delivery device when the further movable element is in one of the first and second positions, wherein the sensor device comprises a sensing arrangement overlying the window or aperture and configured to output signals to the circuitry based on which the circuitry is operable to determine whether or not the first part of the further movable element is externally visible through the aperture or window and thereby to determine when the drug dispensing mechanism has been actuated.

The drug delivery device may comprise a second movable element which is rotatable within the device, wherein rotation of the second movable element and movement of the first movable element are interdependent, the second movable element comprising a code provided around a portion of its exterior, a part of the code being externally visible through a window or aperture formed in the drug delivery device and wherein the sensor device comprises a sensing arrangement overlying the window or aperture and configured to read the portion of the code that is externally visible through the window or aperture, the circuitry being configured to determine, based on the externally visible portion of the code and the position along the path of the first movable element, information relating to drug dose to which the drug delivery device is currently dialled.

BRIEF DESCRIPTION OF THE FIGURES

For a more complete understanding of example embodiments of the present disclosure, reference is now made to the following description taken in connection with the following Figures, in which:

FIGS. 2A to 2E are illustrative simplified views of various components, and combinations of components, of a drug delivery device such as that of FIG. 1 with which a sensor device according to various embodiments may be used;

FIGS. 6A to 6C are illustrative simplified views of various components of an alternative drug delivery device with which sensor devices according to various embodiments of the disclosure may be used;

FIG. 7 is simplified block diagram of a sensor device according to embodiments of the disclosure;

FIG. 8 shows an example of a physical arrangement of the components of the sensor device depicted in FIG. 7;

FIG. 9 shows the sensor device as depicted in FIG. 8 in situ on a drug delivery device;

DETAILED DESCRIPTION

Figure 1:
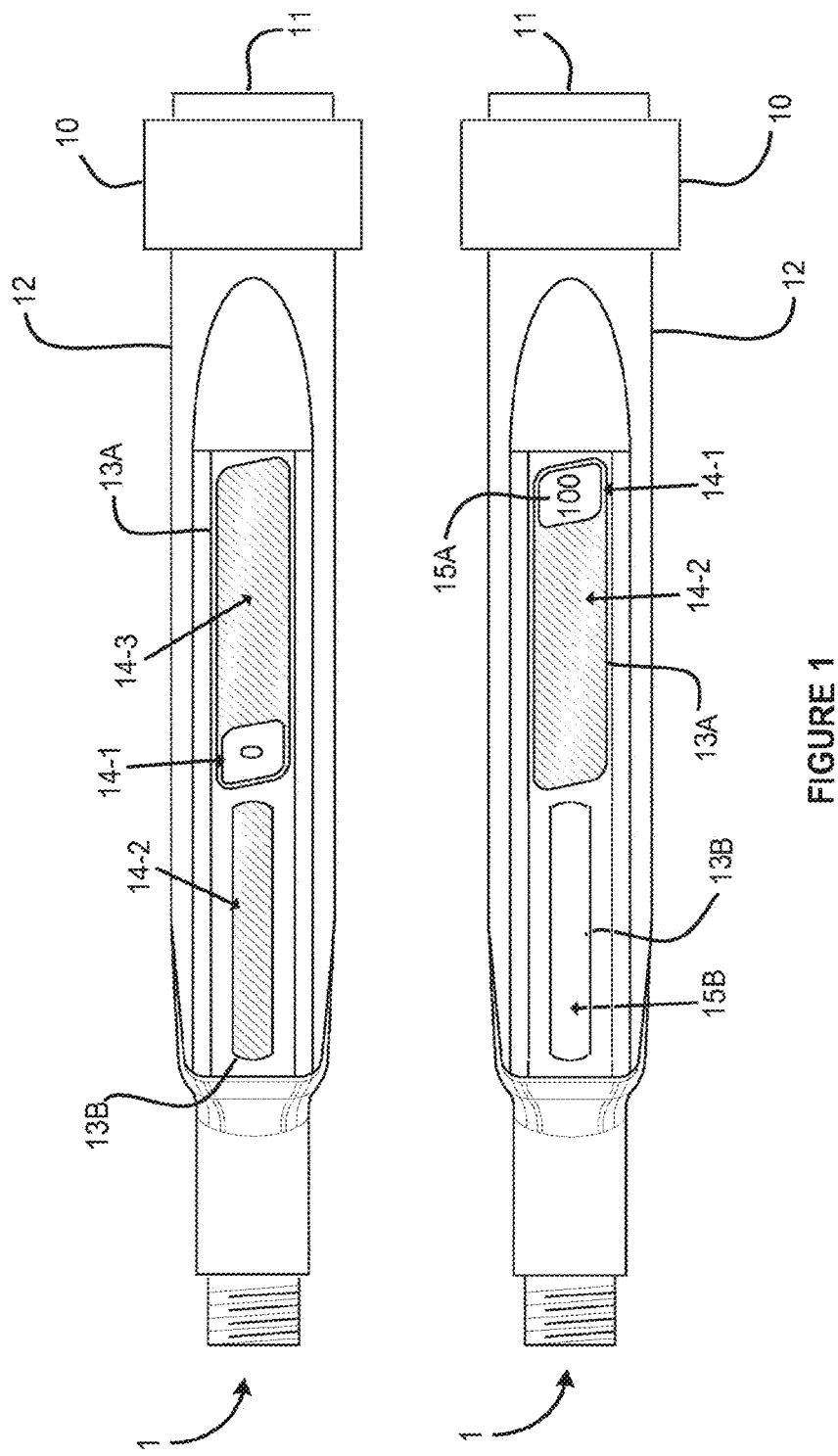
FIG. 1 shows two views of a drug delivery device 1 with which a sensor device according to various embodiments of the disclosure may be used.

In the description and drawings, like reference numerals refer to like elements throughout.

FIG. 1 shows two views of a drug delivery device 1, in this example an injection device, with which a sensor device (also referred to as a supplementary device—not shown) according to various embodiments of the disclosure may be used.

The drug delivery device 1 of FIG. 1 is configured such that a user is able to adjust the drug dosage (or number of drug doses) that is to be delivered (or dispensed) using the device 1. In the example of FIG. 1, this is achieved by rotating (or dialling) a dose selector 10 which causes an internal dialling mechanism (not shown) to adjust an amount of the drug that is to be dispensed once a drug delivery mechanism (not shown) is actuated. In this example, the drug delivery mechanism is actuated by pressing a button 11 on the device.

The drug delivery device 1 comprises an external housing 12 in which is formed at least one aperture or window 13A, 13B. As will be appreciated, an aperture may simply be a cut-away area of the external housing 12, whereas a window may be a transparent portion of the housing through which components of the device may be seen. For convenience, the at least one aperture or window 13A, 13B, will hereafter simply be referred to as the at least one window.

The at least one window 13A, 13B allows a movable gauge element 14 to be visible from the exterior of the housing 12. The drug delivery device is configured such that as the dose selector 10 is dialled, the movable gauge element 14 is caused to be moved thereby to indicate a selected dose to the user. More specifically, as the dose selector 10 is dialled, the gauge element 14 moves axially along an underlying surface 15A, 15B thereby to indicate the selected dose. In the example of FIG. 1, a surface 15A underlying at least part of the gauge element 14 comprises a number sleeve 15A. The number sleeve 15A has numbers indicative of drug doses provided on its outer surface, with the number indicating the currently selected dose being visible through the at least one window 13A, 13B. In this example, the number sleeve 15A is visible through a gauge window (or aperture) 14-1 formed in the movable gauge element. Other parts of the movable gauge element 14 are discussed below.

The uppermost view of the drug delivery device 1 shown in FIG. 1 illustrates the situation before any dialling has been performed. Consequently, the movable gauge element 14 is at its first (or initial) position at a first end of the path along which it is able to move. In this example, when the movable gauge element 14 is at the first end of its path, the portion of the number sleeve 15A that is visible through the gauge window 14-1 shows the number zero (i.e. a zero dose).

The bottommost view of the drug delivery device 1 shown in FIG. 1 illustrates the situation after dialling has been performed. Consequently, the movable gauge element 14 has moved axially along the path that is visible through the first window 13A away from its first position. In this example, the device 1 has been dialled to its maximum dose and as such, the movable gauge element 14 has moved to the second end of its path. The maximum dose in this example is "100" and so the portion of the number sleeve 15A that is visible through the gauge window 14-1 shows the number "100".

In this example, the device 1 comprises first and second windows 13A, 13B. The number sleeve 15A underlies and is visible through the first window 13A, whereas a further underlying element 15B underlies and is sometimes visible through the second window 13B. The further underlying element 15B may or may not include any numbers. The further underlying surface 15B is visually distinguishable from a second part 14-2 of the movable gauge element 14 which overlies it and which is configured to move axially along it. For instance, the second part 14-2 of the movable gauge element 14 may be of a different reflectance to the further underlying surface 15B. For example, one of the gauge element 14 and the underlying surface 15B may be of a light colour (e.g. may be made of a light coloured polymer) and the other may be of dark colour (e.g. may be made of a dark coloured polymer). The user may, therefore, be able to determine the selected dose by determining the proportion of the second window 13A in which the gauge element 14 (specifically, the second part 14-2) is visible compared to the proportion in which the further underlying surface 15B is visible. This can be seen from FIG. 1, in which, when the device 1 is dialled to its zero dose, the gauge element 14 covers the entire length of the path that is visible through the second window 13B. In contrast, when the device 1 is dialled to its maximum dose, none of the gauge element 14 is visible through the second window. Instead, the further underlying surface 15B is visible along the entire length of the path defined by the second window 13B.

The number sleeve 15A (which is also surface underlying the gauge element 14) is also visually distinguishable from the movable gauge element 14 which overlies it and which is configured to move axially along it. For instance, gauge element 14 may be of a different reflectance to the number sleeve 15A. For example, one of the gauge element 14 and the underlying surface 15A may be of a light colour (e.g. may be made of a light coloured polymer) and the other may be of dark colour (e.g. may be made of a dark coloured polymer). In the examples shown in the Figures, the number sleeve 15A and underlying surface 15B are of a higher reflectance than the movable gauge element 14.

FIGS. 2A to 2E are simplified schematics of components of a drug delivery device such as that of FIG. 1. The purpose of FIGS. 2A to 2E is to illustrate the operation of a drug delivery device 1 such as that of FIG. 1; they are not intended to be accurate representations of the exact design of the components.

FIG. 2A is a simplified schematic of the number sleeve 15A. The sleeve 15A has numbers provided on its surface. In some examples, the numbers, ranging from the minimum dose to the maximum dose, may be provided helically around the surface of the number sleeve.

FIG. 2B is a simplified schematic of a movable gauge element 14. The gauge element 14 comprises a first section 14-4 in which the gauge window 14-1 is provided. In this example, the first section is 14-1 a collar which is configured to encircle the number sleeve 15A (as can be seen in FIGS. 2C and 2D). Extending in opposite directions from the first section 14-4 are the second part 14-2 and a third part 14-2. The second and third parts 14-2, 14-3 extend generally parallel to the longitudinal axis of the number sleeve.

The second part 14-2 of the movable gauge element is configured to extend from the first part 14-2 by a length sufficient to fill the entire second window 13B when the movable gauge is in its first position. The second part 14-2 may also serve to obscure a portion of the exterior surface of the number sleeve 15A, when the gauge element moves away from its first position. The third part of the movable gauge element 15-3 is configured to obscure a portion of the exterior surface of the number sleeve 15A, when the gauge elements moves between its first and second positions. In this way, only the portion of the number sleeve that underlies the gauge window 14-1 is visible through the first window 13A of the device housing 12.

The number sleeve 15A is rotatable about its longitudinal axis within the device housing 12. As such, the number sleeve 15A may be referred to as a movable (or rotatable) element. Rotation of the number sleeve 15A is in some embodiments caused by rotation of the dose selector 10.

The rotational movement $NS_R$ of the number sleeve 15A and axial movement $G_E$ of the gauge element 14 are interdependent. Put another way, the dialling mechanism of the device 1 is configured such that when number sleeve 15A is caused to rotate, the gauge element 14 is caused to move or translate axially along its path. Moreover, the degree of rotation of the number sleeve 15A corresponds proportionally to the extent of axial movement of the gauge element 14.

Figure 2E:
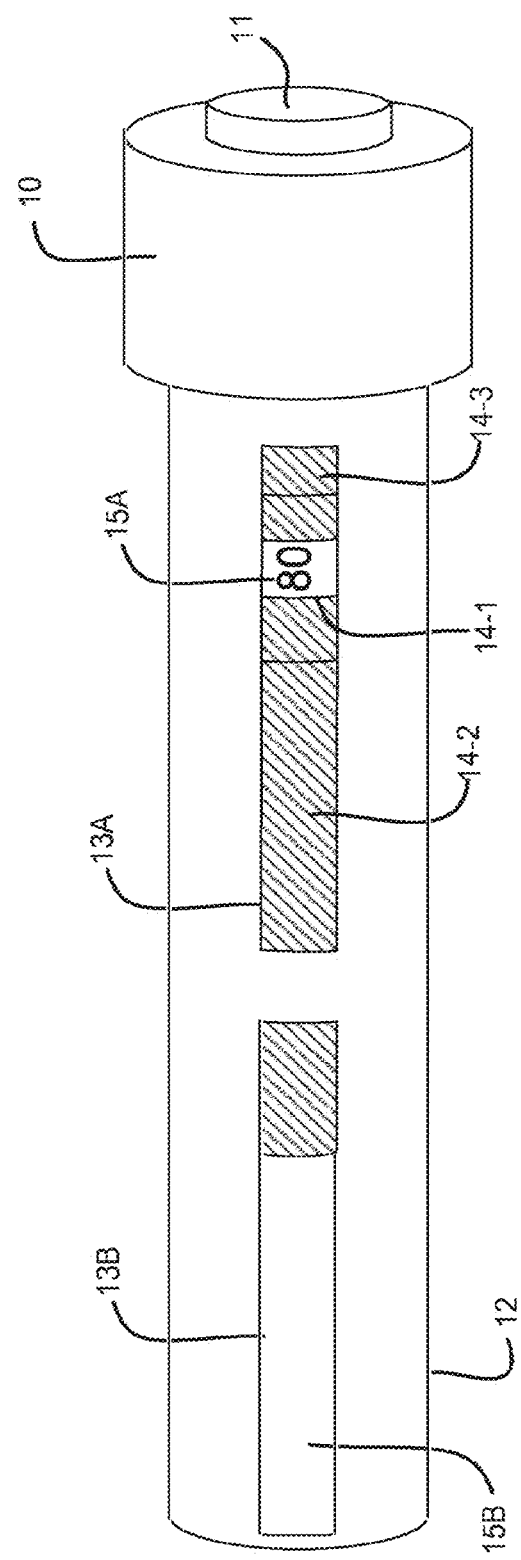

FIG. 2C shows the gauge element 14 in its initial position in which, in this example, it indicates a zero dose. FIG. 2D shows the number sleeve 15A and gauge element 14 following rotation of the number sleeve 15A and translation of the gauge element 14 from its first position. FIG. 2E shows this arrangement of FIG. 2D within a simplified version of the device housing 12.

Various dialling mechanisms for adjusting a dose to be delivered to a user which transform rotation of a dose selector 10 into rotational movement of a number sleeve 15A and axial movement of a gauge element 14 (as described above) are known in the art. Two such mechanisms are described in WO2013/110538A1 and WO2008/145171A1. As such mechanisms (and also drug delivery mechanisms which cause delivery of the drug once the dose has been dialled) are known in the art, they will not be described herein in any detail.

Figure 3:
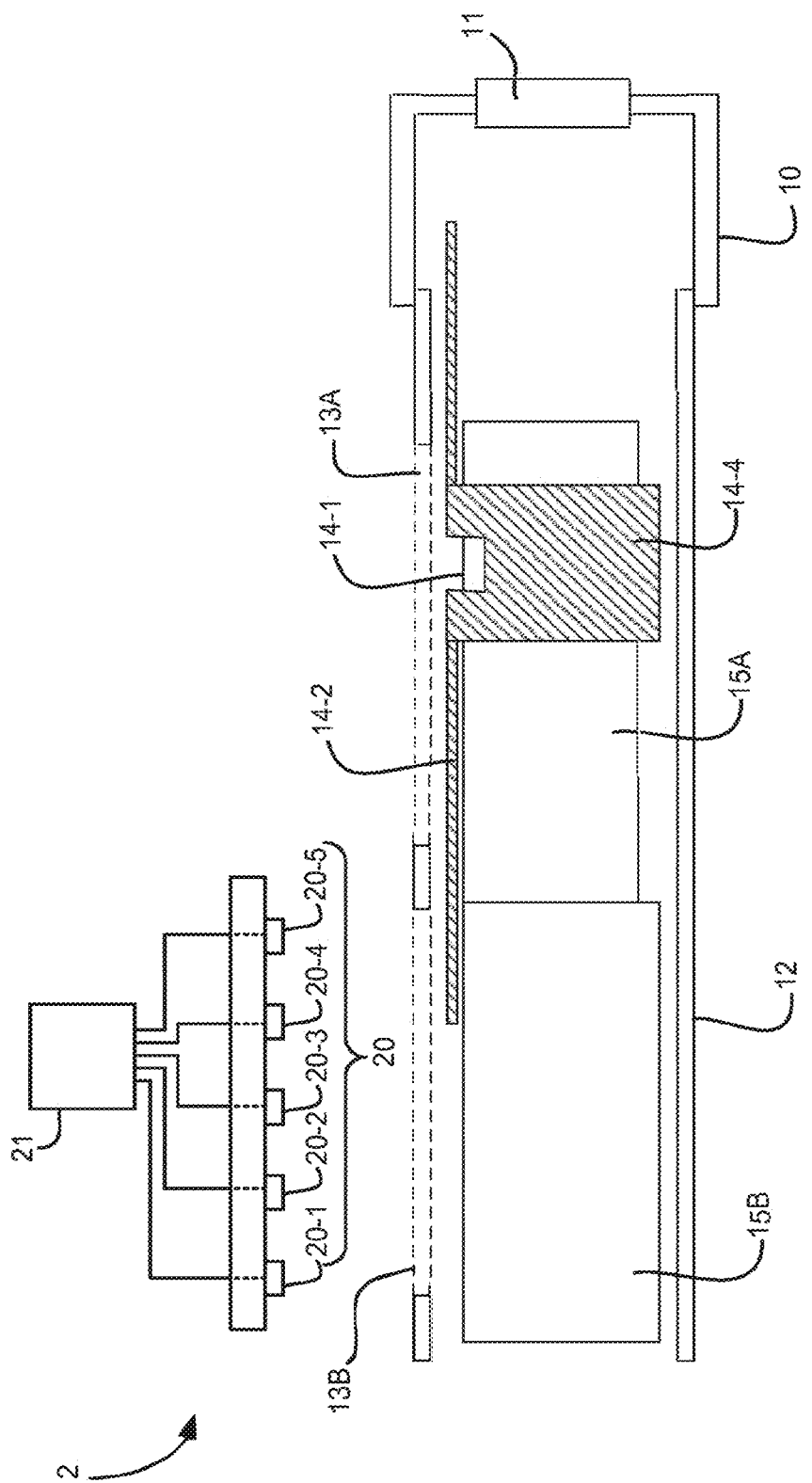
FIG. 3 shows is a simplified cut-away view of the drug delivery device components depicted in FIG. 2D in combination with part of a sensor device according to various embodiments of the disclosure.

FIG. 3 shows an extremely simplified cut-away view of the components of the delivery device 1 as depicted in FIG. 2D and a simplified schematic illustration of a sensor device 2 for use with a delivery device 1 such as that described with reference to FIGS. 1 to 2D.

The sensor device 2 comprises an array 20 of optical sensors 20-1 to 20-5 arranged such that, when the sensor device 2 is in place on the drug delivery device 1, each optical sensor 20-1 to 20-5 in the array 20 is operable to detect light received from a different location along an externally visible path defined by one of the at least one window 13A, 13B. Each optical sensor 20-1 to 20-5 then outputs a signal indicative of an amount of detected light.

The sensor device 2 further comprises circuitry 21 configured to receive the signals output from the optical sensors 20-1 to 20-5 of the array 20 and, based on the received signals, to determine information associated with a location along the path defined by the window 13A, 13B of the movable gauge element 14. The circuitry 21 may be further configured to control operation of the array 20.

When the sensor device 2 is in place adjacent an externally visible path of the drug delivery device 1, the optical sensors 20-1 to 20-5 of the array 20 are spaced along the path. The optical sensors 20-1 to 20-5 may be substantially equidistantly spaced from one another along a length generally corresponding to the length of the visible path. The length over which the optical sensors 20-1 to 20-5 are spaced may not be exactly the same as the length of the visible path along which the gauge element 14 moves but may be dependent on the length of the visible path with which the sensor device 2 is designed to be used.

In some embodiments, the array 20 of optical sensors 20-1 to 20-5 extends generally along an axis which, when the sensor device 2 is coupled to the delivery device 2, is generally parallel with the axis along which the moveable gauge element 14 is configured to move. The axis along which the array 20 of optical sensors extends is therefore also generally parallel with the longitudinal axis of the window 13A, 13B that it overlies. The axis along which the array 20 extends is also generally parallel to the longitudinal axis of the drug delivery device 1. The optical sensors 20-1 to 20-5 may be equidistantly spaced from one another along the axis.

Each of the optical sensors 20-1 to 20-5 has a corresponding light source (not shown) arranged to emit light towards the externally visible path (defined by the window 13A, 13B) when the sensor device 2 is attached to the drug delivery device 1. The light emitted by each light source is then reflected off the visible path back to the corresponding optical sensor 20-1 to 20-5. Each optical sensor 20-1 to 20-5 may be provided in a single package with its corresponding light source. Each of the optical sensors 20-1 to 20-5 may comprise a PIN photodiode, for example. Each of the light sources may, for instance, comprise an LED.

Because the visible path towards which the array 20 is oriented is formed by the gauge element 14 and/or the underlying element 15A, 15B, which are visually distinguishable from one another (e.g. because they are different colours), the amount of light reflected back to each of the optical sensors 20-1 to 20-5 will vary in dependence on the position of the movable gauge element 14 along its path.

The optical sensors of the array 20 may be configured such that, when the amount of detected light is one-side of a threshold, an output signal having a first value is provided to the circuitry 21 and, when the amount of detected light is on the other side of the threshold, an output signal having a second value is provided to the circuitry. In examples in which the optical sensors 20 are PIN photodiodes, when the amount of detected light is below a threshold, the output signal is LOW and when the detected light is above the threshold, the output is HIGH. As will be appreciated the exact threshold of the optical sensors and the values of the signals output by the sensors may be dependent on a number of factors including, for example, the bias applied to the sensors.

The drug delivery device 1 may be configured such that either one of the underlying surface 15A, 15B and the movable gauge element 14 has a reflectance which is sufficiently low such that the light reflected therefrom falls on one side of the sensor threshold. The other one of the underlying surface 15A, 15B and the movable gauge element 14 has a reflectance which is sufficiently high such that the light reflected therefrom falls on the other side of the threshold. In the examples described herein, the underlying surface 15A, 15B has a sufficiently high reflectance to overcome the sensor threshold, whereas the movable gauge element 14 has a sufficiently low reflectance so as not to surpass the sensor threshold. Consequently, in examples in which the sensors 20-1 to 20-5 are PIN photodiodes, sensors located above a section of path at which the gauge element 14 is externally visible output a LOW signal, whereas sensors located above a section of path at which the underlying element 15A, 15B is visible output a HIGH signal.

Figure 4A:
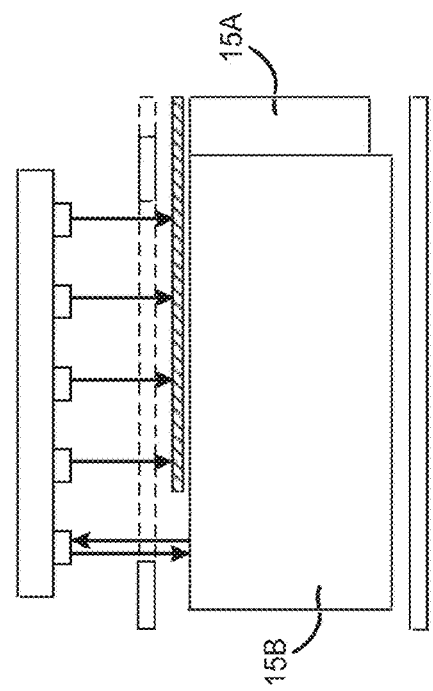
FIGS. 4A to 4D show various views of the drug delivery device and the sensor array of the sensor device of FIG. 3 for the purpose of illustrating the operation of the sensor device.
Figure 4B:
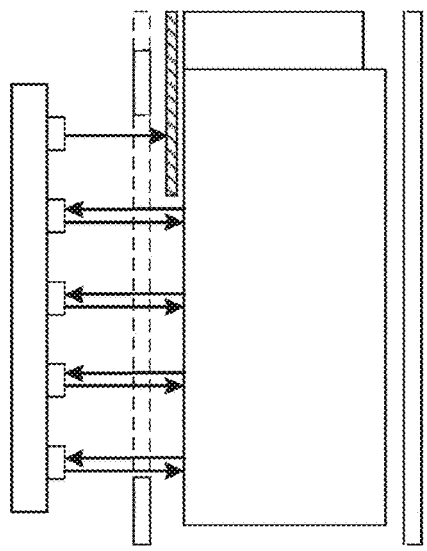
Figure 4C:
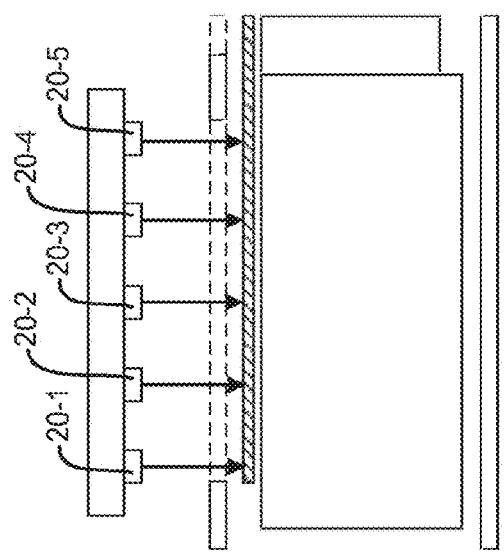
Figure 4D:
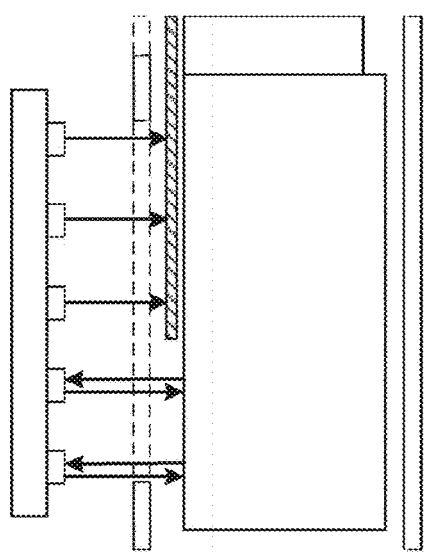

FIGS. 4A and 4D illustrate the operation of the sensor device 2 when the movable element is at different positions along its path. In this example, the array 20 comprises first to fifth optical sensors 20-1 to 20-5, with the first sensor 20-1 being located above a first end of the window 13B at which the movable gauge element 14 is present only when the minimum dose is dialled. The fifth sensor 20-5 is located above a second end of the window 13B at which the gauge element 14 is visible/present unless the maximum dose is dialled.

In FIG. 4A, the movable gauge element 14 is at its initial position (e.g. when the dose is at its minimum). Consequently, the dark coloured (and low reflectance) gauge element 14 covers the entire path underlying the array 20. As such, a sufficient quantity of light to surpass the threshold is not detected by any of the sensors 20-1 to 20-5. As such, all five sensors 20-1 to 20-5 output a LOW signal.

In FIG. 4B, the gauge element 14 has moved to approximately the 20% dose position. In this situation, the light coloured (and high reflectance) underlying surface 15B is visible to the first sensor 20-1. Consequently, sufficient light to surpass the threshold is reflected back from the underlying surface 15B to the first sensor 20-1 and so the first sensor outputs a HIGH signal.

As the gauge element 14, is below each of the other sensors 20-2 to 20-5, these output a LOW signal.

In FIG. 4C, the gauge element 14 has moved to approximately the 40% dose position and so the light coloured (and high reflectance) underlying surface 15B is visible to the first and second sensors 20-1, 20-2, which therefore output a HIGH signal. The third to fifth sensors 20-3 to 20-5 output a LOW signal.

Finally, in FIG. 4D, the gauge element 14 has moved to approximately the 80% dose position and so the light coloured (and high reflectance) underlying surface 15B is visible to the first to fourth sensors 20-1 to 20-4, which output a HIGH signal. The fifth sensor element outputs a LOW signal.

From the above, it is clear how the signals output from the optical sensors 20-1 to 20-1 can be used by the circuitry 21 to determine the dialled dose. This is illustrated in Table 1 below:

TABLE 1

| Determined Dose | $1^{st}$ sensor output | $2^{nd}$ sensor output | $3^{rd}$ sensor output | $4^{th}$ sensor output | $5^{th}$ sensor output |
|---|---|---|---|---|---|
| 0% | LOW | LOW | LOW | LOW | LOW |
| 20% approx. | HIGH | LOW | LOW | LOW | LOW |
| 40% approx. | HIGH | HIGH | LOW | LOW | LOW |
| 60% approx. | HIGH | HIGH | HIGH | LOW | LOW |
| 80% approx. | HIGH | HIGH | HIGH | HIGH | LOW |
| 100% | HIGH | HIGH | HIGH | HIGH | HIGH |

Figure 5:
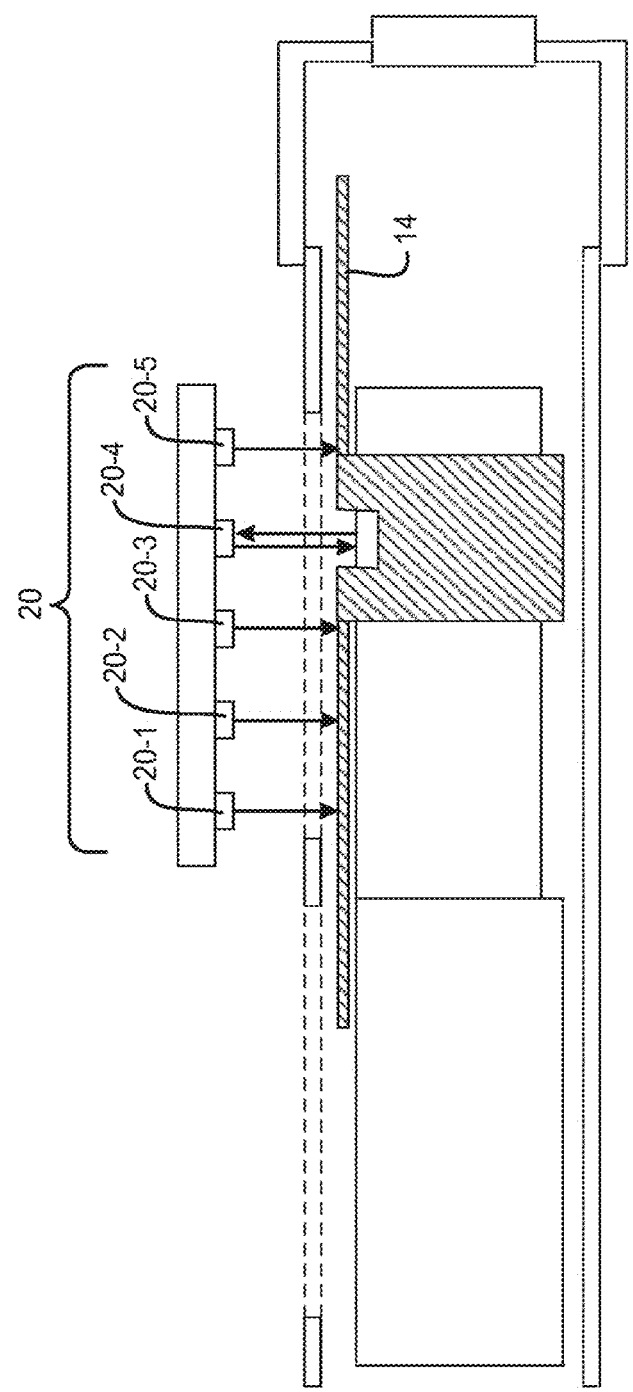
FIG. 5 shows a different arrangement of the sensor array relative to the drug delivery device to that shown in FIGS. 3 and 4A to 4D.

FIG. 5 shows an alternative position of the array of optical sensors 20 with respect to the delivery device 1 to that shown in FIGS. 3 and 4A to 4D. More specifically, in FIG. 5, the sensor array 20 is positioned to overlie the first window 13A, through which the number sleeve 15 is visible via the gauge window 14-1. When used in this configuration, all of the optical sensors 20-1 to 20-5 will provide the same output except that overlying the current location of the gauge window 14-1. This is because, in the first window, the gauge element 14 fills the entire window except for the part at which the gauge window 14-1 is positioned. As such, where the gauge element 14 is of low reflectance compared to the number sleeve 15B, only the sensor element located above the gauge window 14-1 will detect sufficient light to surpass its threshold. In the example of FIG. 5, the circuitry 21 may be configured to determine the location of the movable element 14 within the first window 13A based on the signals output by the sensors in the array, as shown in Table 2:

TABLE 2

| Determined Dose | $1^{st}$ sensor output | $2^{nd}$ sensor output | $3^{rd}$ sensor output | $4^{th}$ sensor output | $5^{th}$ sensor output |
|---|---|---|---|---|---|
| 0% approx | LOW | LOW | LOW | LOW | LOW |
| 20% approx. | HIGH | LOW | LOW | LOW | LOW |
| 40% approx. | LOW | HIGH | LOW | LOW | LOW |

TABLE 2-continued

| Determined Dose | 1st sensor output | 2nd sensor output | 3rd sensor output | 4th sensor output | 5th sensor output |
|---|---|---|---|---|---|
| 60% approx. | LOW | LOW | HIGH | LOW | LOW |
| 80% approx. | LOW | LOW | LOW | HIGH | LOW |
| 100% approx. | LOW | LOW | LOW | LOW | HIGH |

Although the above examples describe optical sensors having a threshold and two distinct outputs (HIGH and LOW), it will be appreciated that sensors which do not have such a threshold and which instead output a signal from which the amount of detected light is derivable (e.g. because the output signal is proportional to the amount of light detected) may instead be used. In such examples, the circuitry 21 is still configured to determine, based on the received signals, whether the movable gauge element 14 or the underlying surface 15A, 15B is visible to a particular optical sensor.

As will be appreciated, the accuracy with which the dose can be determined using the array 20 of optical sensors 20-1 to 20-5 is limited by the number of sensors in the array, with a higher number of sensors providing a higher accuracy. An alternative mechanism for improving the accuracy of the sensor device 2 (instead of simply increasing the number of sensors in the array 20) is discussed with reference to FIGS. 6A to 6D.

FIG. 6A shows an example of a rotatable element 65A, in this instance a number sleeve 65A, which may form part of a drug delivery device 6 for use with sensor devices 1 according to embodiments of the disclosure. FIGS. 6B and 6C show two different simplified views of a delivery device 6 including the rotatable element 65A of FIG. 6A. The delivery device of FIGS. 6 and 6A may be generally the same as that described with reference to the previous figures except for the differences described below.

As with the previously described delivery device 1, the rotation of the rotatable element 65A is interdependent with the axial movement of the movable gauge element 14. The degree of rotation may be proportional to the axial movement of the movable gauge element 14. In the examples of FIG. 6A, the rotatable element 65A has, provided around its exterior surface, a visually-distinguishable code 66 for allowing its rotational orientation to be determined. For instance, the code may enable determination by the sensor device 2 as to whether the rotational orientation is zero degrees, 90 degrees, 180 degrees, 270 degrees. A rotation of zero degrees corresponds to the initial orientation of the rotatable element 65A when the dose of the delivery device 6 is dialled to its minimum. It also corresponds to the orientation after every complete rotation of the rotatable element 65A. In other examples, the code 66 may allow a higher or lower accuracy with regards the rotational orientation of the rotatable element 65A. For instance, the code 66 may allow an accuracy of the 30 or 45 degrees or may allow an accuracy of only 180 degrees. The code 66 may take any suitable form so long as it allows the rotational orientation of rotatable element to be determined by the sensor device 2. In this example, the code 66 is provided at an end of the number sleeve 65A.

The housing 12 of the drug delivery device 6 includes a further aperture or window 63 through which a portion of the rotatable element 65A, on which part of the code 66 is provided, is visible. The further window 63 is positioned and oriented relative to the rotatable element 65A such that a portion of the code is externally visible through the further window 63 regardless of the rotational orientation of the rotatable element 65A. The further window 63 is positioned and oriented relative to the rotatable element 65A such that, as the rotatable element rotates through a single complete rotation, a different section of the code 66 is visible at each rotational orientation. The further aperture is, in this example, provided on a different side of the device housing 12 (or, if the housing is cylindrical or otherwise rounded, around the exterior surface of the device housing 12) from the at least one window 13A, 13B through which the movable gauge element 14 is visible. In this way, the movable gauge element 14 does not obstruct the code from view.

Figure 6D:
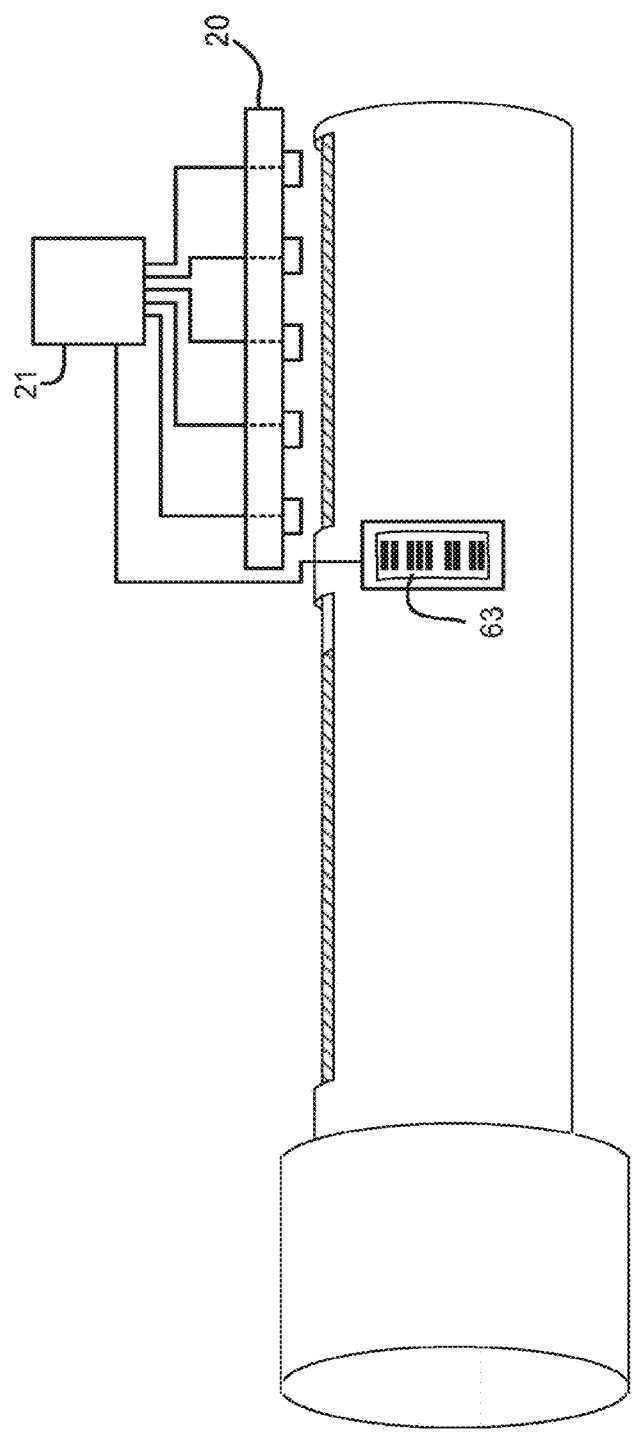
FIG. 6D is a simplified view of a sensor device according to embodiments of the disclosure in combination with the drug delivery device of FIGS. 6A to 6C.

As shown schematically in FIG. 6D, the sensor device 2 may, in addition to the array 20 of optical sensors 20-1 to 20-5, include a further sensing arrangement 23. The sensing arrangement 23 is arranged within the sensor device 2 such that, when the sensor device 2 is attached to the drug delivery device 6, the sensing arrangement 23 is operable to read encoded information 660 (which may include the code 66) that is externally visible on the drug delivery device 6. In this example, at least part of the encoded information 660 is visible through the further window 63. In some other examples, such as are discussed below, at least part of the encoded information may be provided on a portion of the exterior of the housing 12 which underlies the sensing arrangement 23.

The sensing arrangement 23 may be of any suitable type as long as it enables the encoded information 660 to be read. For instance, the sensing arrangement may be an optical sensing arrangement comprising a camera or a small array of sensing elements, a magnetic or inductive sensing arrangement or a conductance/resistance sensing arrangement.

The circuitry 21 of the sensor device 2 of FIG. 6D is configured to determine, based on the encoded information 660, information relating to operation of the drug delivery device 6. In some specific examples, the circuitry 21 is configured to determine a current dose to which the device 6 is dialled, based on the encoded information 660 and the signals output from the optical sensors of the array 20. For instance, the signals output from the array 20 may be utilised by the circuitry 21 to determine the number of complete rotations of the rotatable element 65A that have occurred and the encoded information 660 read by the sensing arrangement 23 may be utilised to determine the rotational orientation of the rotatable element 65A. Put another way, the signals output from the array 20 may be used to determine roughly the extent of axial translation of the moveable gauge element, with the encoded information 660 read by the sensing arrangement being used with the rough determination to more precisely determine the extent of translation of the movable gauge element 14 (thereby to determine the currently dialled dose).

The array 20 may comprise the same number of optical sensors 20-1 to 20-5 as the number of complete rotations of the rotatable element 65A that are required to move the movable gauge element 14 from its initial to final position. The sensors 20-1 to 20-5 may be distributed adjacent the visible path of the movable gauge element such that after every complete rotation of the rotatable element 65A, the output of a successive optical sensor in the array 20 changes. For instance, using the example described with reference to FIGS. 4A to 4D and Table 1, after the first complete rotation of the rotatable element 65A, the output of the first sensor 20-1 in the array 20 changes from LOW to HIGH. After the second rotation, the output of the second sensor 20-2 changes from LOW to HIGH. After the third complete rotation, the output of the third sensor 20-2 changes from LOW to HIGH and so on until the fifth complete rotation at which point the output of the fifth sensor 20-5 changes from LOW to HIGH. It will thus be appreciated that the signals output by the sensors of the array 20 can be used to determine the number of complete rotations.

The encoded information 660 (specifically, code 66) read by the sensing arrangement 23 is then used by the circuitry 21 to determine the extent of any partial rotations of the rotatable element 65A. The determined extent of partial rotation of the rotatable element 65A is then combined with the determined number of complete rotations to determine the currently dialled dose of the drug delivery device 6. This determination is illustrated in Table 3 below:

TABLE 3

| Dose | 1st sensor output | 2nd sensor output | 3rd sensor output | 4th sensor output | 5th sensor output | Partial Rotation (degrees) |
|---|---|---|---|---|---|---|
| 0% | LOW | LOW | LOW | LOW | LOW | 0 |
| 10% | LOW | LOW | LOW | LOW | LOW | 180 |
| 20% | HIGH | LOW | LOW | LOW | LOW | 0 |
| 30% | HIGH | LOW | LOW | LOW | LOW | 180 |
| 40% | HIGH | HIGH | LOW | LOW | LOW | 0 |
| 50% | HIGH | HIGH | LOW | LOW | LOW | 180 |
| 60% | HIGH | HIGH | HIGH | LOW | LOW | 0 |
| 70% | HIGH | HIGH | HIGH | LOW | LOW | 180 |
| 80% | HIGH | HIGH | HIGH | HIGH | LOW | 0 |
| 90% | HIGH | HIGH | HIGH | HIGH | LOW | 180 |
| 100% | HIGH | HIGH | HIGH | HIGH | HIGH | 0 |

It will be understood that the accuracy of the sensor device 2 can be improved by increasing the accuracy with which partial rotations can be determined. For instance, in the above example, if quarter rotations (i.e. every 90 degrees) were instead identifiable, the circuitry 21 would be able to determine the dialled dose to an accuracy of 5%.

Up until now, the composition of the electronic device 2 has been described at a very high level. FIGS. 7, 8 and 9 depict the sensor device 2 in more detail.

FIG. 7 is a simplified schematic block diagram of a sensor device 2 according to various embodiments. As described above, the sensor device 2 comprises the array 20 of optical sensors 20-1 to 20-5 which are configured to output signals to the circuitry 21. In some embodiments, the device 2 comprises the further sensing arrangement 23 which is configured to output signals indicative of the encoded information to the circuitry 21.

The circuitry 21 may be of any suitable composition and may comprise any combination of one or more processors and/or microprocessors 210 (for simplicity, hereafter referred to as "the at least one processor") suitable for causing the functionality described herein to be performed.

The circuitry 21 may additionally or alternatively comprise any combination of one or more hardware-only components such as ASICs, FPGAs etc. (which are not shown in FIG. 7).

The circuitry 21 may further comprise any combination of one or more non-transitory computer readable memory media 211, such as one or both of ROM and RAM, which is coupled to the at least one processor 210. The memory 211 may have computer-readable instructions 211A stored thereon. The computer readable instructions 210, when executed by the at least one processor 210 may cause the sensor device 2 to perform the functionality described in this specification, such as controlling operation of the array 20 and sensing arrangement 23 and interpreting the signals received therefrom.

The sensing arrangement 23 comprises at least a light source 23-2 and a photosensor 23-1. The light source 23-2 is for illuminating the encoded information 66 that is visible within the further window 63 formed in the device housing 62. The photosensor 23-1 is configured read the encoded information by detecting an image (which includes the encoded information 660) which is visible to the photosensor (i.e. which underlies the photosensor). The image is detected by detecting the light reflected back from different parts of the surface(s) on which the image is provided. The encoded information 660 is then passed to the circuitry 21. The sensing arrangement 23 may comprise further non-electrical components, which are not shown on FIG. 7. These non-electrical components of the sensing arrangement 23 are described with reference to FIG. 8.

The sensor device 2 may further comprise one or both of a display screen 24 (such as an LED or LCD screen) and a data port 25. The display screen 24 may be operable under the control of the circuitry 21 to display information regarding operation of the drug delivery device 1 to the user. For instance, the information determined by the sensor device 2 may be displayed to the user. The information determined by the sensor device 2 may include the dialled dose. Other information which can be determined by the sensor device 2 includes the drug being dispensed, the mode of the drug delivery device 1, 6, and or a history of previously-dispensed doses. The determination of this "other information" is discussed below with respect to FIGS. 10A, 10B and 11.

The data port 25 may be used to transfer stored information relating to the operation of the drug delivery device 6 from the memory 211 to a remote device such a PC, tablet computer, or smartphone. Similarly, new software/firmware may be transferred to the sensor device via the data port 25. The data port 25 may be a physical port such as a USB port or may be a virtual, or wireless, port such as an IR, WiFi or Bluetooth transceiver.

The sensor device 2 may further comprise a removable or permanent (preferably rechargeable with e.g. photovoltaic cells) battery 26 for powering the other components of the device 2. Instead of the battery 26, a photovoltaic or capacitor power source may be used. Other electrical components which are not shown in FIG. 7, but which may nonetheless be included in the sensor device 2 include a trigger buffer 27-1, a regulator 27-2, a voltage suppressor 27-3 and a charger chip 27-4, for charging the rechargeable battery if present.

FIG. 8 shows an example of a physical arrangement of the components of the sensor device of FIG. 7. The optical sensors 20-1 to 20-5 of the array 20 are arranged on a first surface of a PCB 28-1 in a way that is determined by the shape of the visible path of the movable element 14 with which the sensor device 2 is designed to be used. In the examples described herein, the visible path is linear and, consequently, the optical sensors 20-1 to 20-5 of the array 20 are linearly arranged on the PCB 28-1. When the sensor device 2 is attached to the drug delivery device 1, 6, the first surface of the PCB 28-1 faces the at least one window 13A, 13B of the drug delivery device 1, 6.

One or more of: the light source 23-2 of the sensor arrangement 23, the at least one processor 210, the memory 211, the charger chip 27-4, the voltage suppressor 27-3, the regulator 27-2 and the trigger buffer 27-1 may also be provided on the first surface of the PCB 28-1.

The screen 24 is provided on the opposite side of the PCB to the 28-1 to the array 20 of optical sensors 20-1 to 20-5, such that it is visible to the user when the sensor device 2 is attached to the drug delivery device 1, 6. The sensor device 2 may be configured so as to extend over the entire area of the at least one window 13A, 13B such that the at least one window 13A, 13B is not visible to the user when the sensor device 2 is attached.

When the drug delivery device 6 includes the further window 63 which is located on a different side of the device housing 62 to the at least one window 13A, 13B in which the movable gauge element 14 is visible, the photosensor 23-1 of the sensing arrangement 23 may not be provided on the PCB 28-1. Instead, the photosensor 23-1 may be provided on a support element 28-2 which extends from the PCB 28-1. In the example of FIG. 1, the support element 28-2 extends perpendicularly from the PCB, such that when it is attached to the drug delivery device 6, it wraps around a side of the device 6.

As will be appreciated the exact physical arrangement of the components within the sensor device 2 may not be crucial as long as, when the sensor device 2 is attached to the drug delivery device 1, 6, the array 20 of optical sensors is aligned with and faces the visible path of the movable element 14. In embodiments including the further sensing arrangement 23, it may also be important that the photosensor 23-1 of the sensing arrangement 23 is positioned so as to overlie further window 63 formed in the housing 12 of the drug delivery device 6.

The sensing arrangement 23, in this example, further comprises a light guide 23-3 for guiding the light from the light source 23-2 to the further window 63 of the drug delivery device 6. The sensing arrangement 23 also comprises a lens array 23-4 for focussing on the photosensor 23-1 the light reflected back from the surface(s) underlying the photosensor 23-1. Put another way, the lens array 23-4 is configured to focus the image, which is provided on the surface(s) underlying the photosensor 23-1, on to the photosensor 23-2.

FIG. 9 shows the sensor device 2, without a housing, in position on the drug delivery device 1, 6. Although not shown, the sensor device 2 may be configured to be removably attached in position on the drug delivery device 1, 6. For instance, the housing (not shown) of the sensor device 2 may include a coupling mechanism for securely affixing the sensor device 2 to the drug delivery device 1, 6. Alternatively, any other means for securing the sensor device 2 in position on the drug delivery device 1, 6 may be used.

As discussed above, the encoded information 660 that is read by the sensing arrangement 23 may include a portion of a code 66 for enabling the circuitry to determine the rotational orientation of the rotatable element 15A, 65A. However, in some embodiments, other operational information may alternatively or additionally be included in the encoded information 660 that is read by the sensing arrangement. For instance, the encoded information 660 may include a portion 67 (for instance in the form of a bar code) for indicating the drug that is being delivered. This can be seen in FIGS. 10A and 10B which show examples of two different views of the encoded information that may be visible to the photosensor of the sensing arrangement 23. At least part of the encoded information 660 (such as the portion of the code 66) may be visible through the further window 63 of the drug delivery device 6. The drug indication code portion 67 may be provided on, for instance, a portion of a drug cartridge that is inserted into the drug delivery device 1, 6 and which is visible through the further window 63 and so can be read by the sensing arrangement 23. Alternatively, it may be provided on a portion of the exterior of the delivery device housing 12 that is adjacent the further window 63 and which is also beneath (and so readable by) the photosensor 23-1 of the sensing arrangement 23 when the sensor device 2 attached to the drug delivery device 1, 6.

Figure 10B:
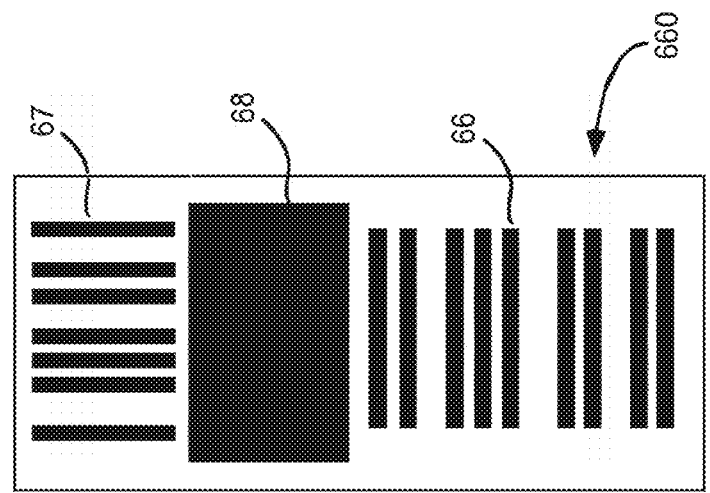
FIGS. 10A and 10B show examples of encoded information which may be read by the sensor device according to various embodiments of the disclosure.
Figure 10A:
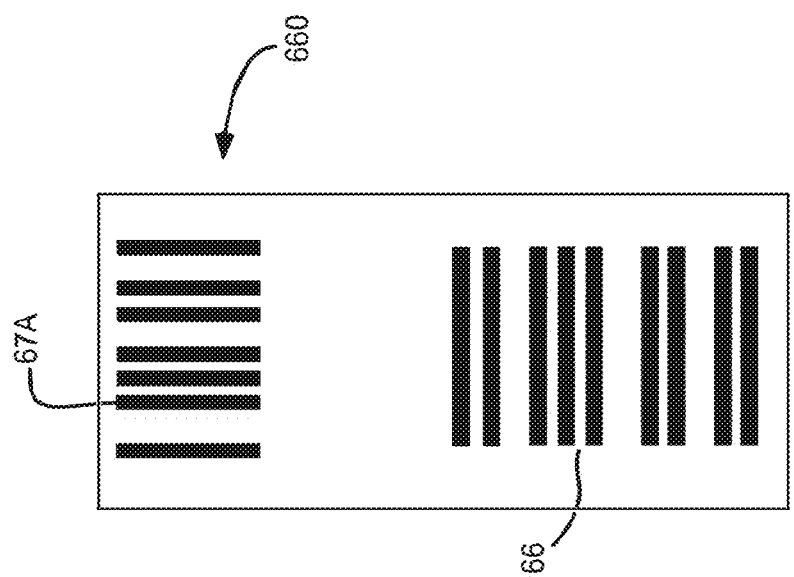

The encoded information 660 may further include a portion 68 for indicating a mode of the drug delivery device 1, 6. This can be seen in FIGS. 10A and 10B which show the encoded information 660 when the device 1, 6 is in each of a dialling mode and delivery mode. In this example, when the device is in the dialling mode, the mode indicator 68 is not part of the encoded information (as shown in FIG. 10B) and when the device in the delivery mode, the mode indicator 68 is part of the encoded information 660. Consequently, by determining whether or not the mode indicator 68 is present in the encoded information 660, the circuitry 21 can determine the mode of the device 1, 6.

Figure 11:
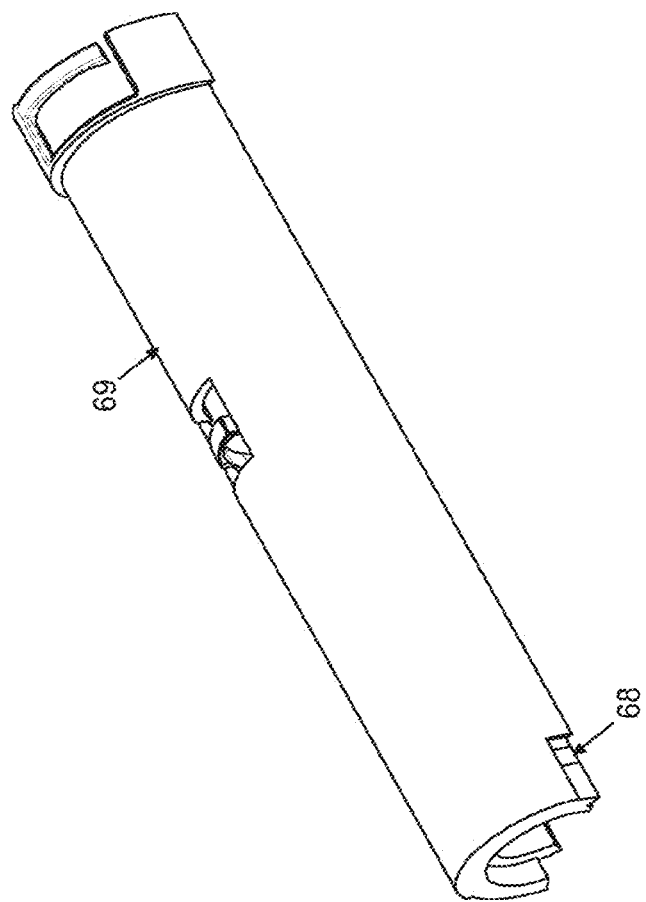
FIG. 11 shows a component of a drug delivery device for use with the sensor device according to various embodiments of the disclosure.

The mode indictor 68 may be provided on an internal element that is caused to move in response to actuation of the drug delivery mechanism (for instance by pushing the button 11). The movable internal element and drug delivery mechanism are together configured such that actuation of the drug delivery mechanism thereby to switch from dialling mode to delivery mode, causes the mode indicator 68 to become visible (or to disappear from) within the further window 63. An example of such an internal movable element 69 is shown in FIG. 11 and is a "locking arm". When situated within the drug delivery device 16, the locking arm 69 is configured to move from a first position to a second position in response to actuation of the drug delivery mechanism. The locking arm 69 may be further configured to move from the second position back to the first position in response to subsequent actuation of the drug dialling mechanism. The mode indicator 68 is only visible through the window 63 when the locking arm 69 is in one of the first and second positions. In this way, the sensor device 2 is able to determine the mode of the drug delivery device 6 to which it is attached.

In some embodiments, the sensor device 2 is configured to store a history of dispensed drug doses. This may be carried out by storing information indicative of the currently dialled dose, when a change from dialling mode to delivery mode is detected based on the mode indicator 68. A timestamp indicative of a time at which the mode change occurred may also be stored in association with the information indicative of the dose. In addition or alternatively, information indicative of the type of the dispensed drug, which is determined based on the drug indication code portion 67, may be stored in association with the dose information. This may be repeated each time a dose of a drug is dispensed Although the drug delivery devices described herein include two windows 13A, 13B through which the movable gauge element 14 is visible, it will be appreciated (particularly from the discussions of FIGS. 4A to 4D and 5) that sensor devices 2 according to embodiments of the disclosure may be used with drug delivery devices 1, 6 which include only one of these windows 13A, 13B.

It should be realized that the foregoing embodiments should not be construed as limiting. Other variations and modifications will be apparent to persons skilled in the art upon reading the present application. Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The invention claimed is:

1. A sensor device removably attachable to a drug delivery device, the sensor device comprising:
   an array of optical sensors arranged within the sensor device, the drug delivery device having a first movable element configured to move along a linear path parallel to a longitudinal axis of the drug delivery device, each optical sensor being operable to detect light received at different locations along the linear path and to output a signal indicative of an amount of detected light when the sensor device is attached to the drug delivery device;
   circuitry configured to receive the signals output from the optical sensors and, based on the received signals, to determine information associated with a location along the linear path of the first movable element; and
   a sensing arrangement arranged within the sensor device, the sensing arrangement being operable to read encoded information that is visible from an exterior of the drug delivery device when the sensor device is attached to the drug delivery device,
   wherein the circuitry is further configured to determine, based on the encoded information, a drug that the drug delivery device is being used to dispense.

2. The sensor device of claim 1, wherein the encoded information comprises a drug indicator portion for indicating the drug that the drug delivery device is being used to dispense.

3. The sensor device of claim 2, wherein the drug indicator portion is visible to the sensing arrangement through an aperture or window formed in the drug delivery device.

4. The sensor device of claim 3, wherein the drug indicator portion is provided on a portion of a drug delivery cartridge that is inserted into the drug delivery device and which is visible through the aperture or window.

5. The sensor device of claim 2, wherein the drug indicator portion is provided on a portion of the exterior of the drug delivery device that is adjacent to an aperture or window formed in the drug delivery device.

6. The sensor device of claim 2, wherein the sensing arrangement is arranged to overly the drug indicator portion when the sensor device is attached to the drug delivery device.

7. The sensor device of claim 2, wherein the drug indicator portion comprises a bar code.

8. The sensor device of claim 1, wherein the circuitry is further configured to determine, based on the encoded information and the location along the linear path of the first movable element, information relating to a drug dose to which the drug delivery device is currently dialed.

9. The sensor device of claim 8, wherein:
   at least part of the encoded information is provided on at least a second movable element of the drug delivery device, the second movable element being rotatable within the drug delivery device; and
   the circuitry is further configured to determine, based on the encoded information, a degree of rotation of the second movable element within the drug delivery device.

10. The sensor device of claim 9, wherein the circuitry is further configured to determine the information relating to a currently dialed drug dose based on the location along the linear path of the first movable element and the degree of rotation of the second movable element.

11. The sensor device of claim 1, wherein the circuitry is further configured to determine, based on the encoded information, whether an operational mode of the drug delivery device is a dialing mode or a delivery mode.

12. The sensor device of claim 1, wherein:
   at least part of the encoded information is visible from the exterior of the drug delivery device through an aperture or window formed in the drug delivery device; and
   the sensing arrangement is arranged within the sensor device such that when the sensor device is attached to the drug delivery device, the sensing arrangement is operable to detect light received from the aperture or window.

13. The sensor device of claim 12, wherein the sensing arrangement comprises:
   a light source arrangement configured to project light towards the aperture or window in the drug delivery device when the sensor device is attached to the drug delivery device; and
   a photosensor arrangement configured to receive light reflected from the aperture or window.

14. A drug delivery system comprising:
   a drug delivery device comprising a first movable element configured to move along a linear path parallel to a longitudinal axis of the drug delivery device; and
   a sensor device attached to the drug delivery device, the sensor device comprising:
      an array of optical sensors arranged within the sensor device, each optical sensor is operable to detect light received at different locations along the linear path and to output a signal indicative of an amount of detected light,
      circuitry configured to receive the signals output from the optical sensors and, based on the received signals, determine information associated with a location along the linear path of the first movable element, and
      a sensing arrangement arranged within the sensor device, the sensing arrangement being operable to read encoded information that is visible from an exterior of the drug delivery device,
   wherein the circuitry is configured to determine, based on the encoded information, a drug that the drug delivery device is being used to dispense.

15. The drug delivery system of claim 14, wherein the drug delivery device comprises a drug indicator portion for indicating the drug that the drug delivery device is being used to dispense.

16. The drug delivery system of claim 15, wherein the drug indicator portion is provided on a portion of a drug delivery cartridge that is inserted into the drug delivery device and which is visible through an aperture or window formed in the drug delivery device.

17. The drug delivery system of claim 14, wherein:
   the first movable element is moveable along an underlying element and is configured such that movement of the first movable element in a particular direction causes the underlying element to become visible from the exterior of the drug delivery device at successive locations along the linear path; and at least part of the first movable element has a first reflectance and the underlying element has a second, different reflectance.

18. The drug delivery system of claim 17, wherein the first moveable element is movable relative to the underlying element such that movement in a first direction along the linear path causes an increasing length of the underlying element to become visible in the linear path.

19. The drug delivery system of claim 14, wherein:

the drug delivery device comprises a second movable element which is rotatable within the drug delivery device;

rotation of the second movable element and movement of the first movable element are interdependent, the second movable element comprising a code provided around a portion of an exterior of the second movable element, a part of the code being visible from an exterior of the drug delivery device through a window or aperture formed in the drug delivery device; and the sensor device comprises a sensing arrangement overlying the window or aperture and configured to read the part of the code that is visible from the exterior of the drug delivery device through the window or aperture, the circuitry being configured to determine, based on the part of the code that is visible from the exterior of the drug delivery device through the window or aperture and a position along the linear path of the first movable element, information relating to drug dose to which the drug delivery device is currently dialed.

20. The drug delivery system of claim 14, wherein the circuitry is further configured to determine, based on the encoded information and the location along the linear path of the first movable element, information relating to a drug dose to which the drug delivery device is currently dialed.

21. The drug delivery system of claim 20, wherein:

at least part of the encoded information is provided on at least a second movable element of the drug delivery device, the second movable element being rotatable within the drug delivery device; and the circuitry is configured to determine, based on the encoded information, a degree of rotation of the second movable element within the drug delivery device.

* * * * *

UNITED STATES PATENT AND TRADEMARK OFFICE
CERTIFICATE OF CORRECTION

| | | |
|---|---|---|
| PATENT NO. | : 11,118,943 B2 | Page 1 of 1 |
| APPLICATION NO. | : 16/785887 | |
| DATED | : September 14, 2021 | |
| INVENTOR(S) | : Matthew Jones et al. | |

It is certified that error appears in the above-identified patent and that said Letters Patent is hereby corrected as shown below:

On the Title Page

Column 1, Line 3 under (72) Inventors:, delete "Warwickshire (DE);" and insert -- Warwickshire (GB); --

Signed and Sealed this
Thirteenth Day of June, 2023

Katherine Kelly Vidal
*Director of the United States Patent and Trademark Office*